(12) United States Patent
Galli et al.

(10) Patent No.: US 7,138,257 B2
(45) Date of Patent: Nov. 21, 2006

(54) METHOD FOR PRODUCING ETHANOL BY USING CORN FLOURS

(75) Inventors: Marco Galli, Cremona (IT); Attilio Veneri, Cremona (IT)

(73) Assignee: Ocrim, S.p.A., Cremona (IT)

( * ) Notice: Subject to any disclaimer, the term of this patent is extended or adjusted under 35 U.S.C. 154(b) by 0 days.

(21) Appl. No.: 11/194,909

(22) Filed: Aug. 1, 2005

(65) Prior Publication Data

US 2006/0035354 A1 Feb. 16, 2006

(30) Foreign Application Priority Data

Aug. 11, 2004 (IT) .......................... MI2004A1646

(51) Int. Cl.
*C12P 7/06* (2006.01)
(52) U.S. Cl. ..................................... 435/161
(58) Field of Classification Search ................ 435/161
See application file for complete search history.

(56) References Cited

U.S. PATENT DOCUMENTS

| | | | |
|---|---|---|---|
| 3,399,839 A | 9/1968 | Anderson et al. | |
| 4,361,651 A | 11/1982 | Keim et al. | |
| 6,254,914 B1 | 7/2001 | Singh et al. | |
| 6,550,700 B1 * | 4/2003 | Griebat et al. | 241/30 |
| 6,740,508 B1 * | 5/2004 | Ulrich et al. | 435/72 |
| 6,953,165 B1 * | 10/2005 | Griebat et al. | 241/11 |
| 2003/0180897 A1 * | 9/2003 | Ulrich et al. | 435/134 |
| 2003/0224496 A1 * | 12/2003 | Jakel et al. | 435/144 |

FOREIGN PATENT DOCUMENTS

EP 1 213 054 A 6/2002

* cited by examiner

*Primary Examiner*—Herbert J. Lilling
(74) *Attorney, Agent, or Firm*—R Neil Sudol; Henry D. Coleman; William J. Sapone

(57) ABSTRACT

A method for producing ethanol starting from corn flours, which provides for the milling of the corn, the separation of the light fractions (bran), a first refining of the milled fractions, a first sifting with germ separation, a second refining of the milled fractions, and a second sifting with germ separation. In particular, according to the invention, impact milling of the wet corn is provided so as to preserve the largest possible average particle size of the milled fractions, and subsequent crushing of the germ is also provided, so as to facilitate size separation thereof. With respect to known systems for producing ethanol starting from corn flours, the method according to the invention allows to extract from corn at least 7%, preferably at least 10% (by weight with respect to the initial product) of pure germ (i.e., germ not contaminated by other components) and at least 1% pure bran, preferably at least 2.5%, before transfer to the ethanol extraction plant, with the previously cited consequent advantages and overcoming the drawbacks that arise from using the systems that constitute the background art. In particular, the extraction from corn of at least 7% of the germ, preferably at least 10%, and of at least 1% bran, preferably at least 2.5%, allows to achieve drastic reductions in the production of pasty residues in the subsequent ethanol extraction process.

16 Claims, 3 Drawing Sheets

METHOD FOR PRODUCING ETHANOL BY USING CORN FLOURS

BACKGROUND OF THE INVENTION

Field of the Invention

The present invention relates to a new improved type of method for producing ethanol by using corn flours.

Ethanol is used mostly in preparing fuels that cause low environmental pollution with respect to gasoline: ethanol burns more completely and is more environmentally friendly. Vehicles operating with 85% ethanol fuel produce lower hydrocarbon and benzene emissions than gasoline-fueled vehicles and can also reduce the input of carbon dioxide, a gas that is responsible for the greenhouse effect and the main cause of global warming, into the atmosphere.

Although carbon dioxide is released during ethanol production and combustion, it is in fact recaptured as a nutrient by the corn used for its production, and differently from the combustion of fossil fuels, which releases carbon that has remained stored for millions of years, the use of ethanol leads to a reduced increase in the carbon cycle. Moreover, ethanol degrades rapidly in water and therefore entails lower environmental risks than Diesel fuel or gasoline.

Accordingly, ethanol-based fuels are commonly defined as "renewable plant-derived fuels" and can be used effectively both in the pure state and mixed with fossil Diesel fuel: mixtures of fuels based on ethanol with fossil Diesel fuel are commonly known as biodiesel. Biodiesel can be used effectively also as a heating fuel.

Publications on the subject report that several studies have demonstrated that the use of 1 kg of biodiesel entails a reduction, with respect to the use of a corresponding amount of fossil fuel, of approximately 3 kg of carbon dioxide: its use accordingly leads to a significant reduction in gas emissions, particulate emissions and emissions of other dangerous components.

Other advantages arise from the fact that ethanol-based fuels have an extremely low sulfur content and a high lubricating power and are rapidly biodegradable.

As a confirmation of the true interest that ethanol-based fuels are receiving, mention is made of European directive 2003/30/CE on the promotion of biofuels, which suggests that Europe should strive to cover, by 2010, 5.75% of the fuel market with non-polluting alternatives based on ethanol or plants.

Ethanol can be extracted from corn with a chemical process performed in appropriately provided plants.

The source cereal is pretreated according to two different technologies, which constitute the currently known methods for preparing corn intended for subsequent ethanol extraction and are termed respectively "wet mill" and "dry mill".

The "wet mill" process begins with a step for macerating the whole corn in water, acidified with $H_2SO_4$ at pH 5.8 for 48 hours. The product is then transferred to a so-called pin mill, which allows to separate the germ in percentages on the order of 4%. The fiber (bran) is separated in a subsequent washing step, while appropriate centrifugation separates the starch, which enters the ethanol production process described hereafter. The process for preparing corn intended for ethanol production known as "wet mill" is not particularly widespread. Substantially, it entails macerating the whole corn, milling the corn in a pin mill, washing the milled corn, separating the fibers and centrifuging the washed product, thus obtaining a cereal that has a high content of starches and is designed to be sent to the ethanol extraction plant.

The "dry mill" treatment, instead, consists in milling, performed with a hammer mill, and subsequent maceration. It is currently a more widely used technology.

The main purpose of these plants is obviously to extract ethanol, while the step for drying the residues is performed only in order to be able to reuse the residues. In other words, the operators of plants for producing ethanol from pretreated corn would prefer to be able to obtain mostly ethanol, minimizing the production of pasty residues, which require the use of the expensive step of the process that consists in drying them.

The component of corn from which ethanol is obtained by means of the chemical process described above is starch, while the other components of the cereal (bran and germ) are the main factors that contrast optimization of the yield of the steps of the ethanol extraction process and in particular cause, in the process, the production of the unwanted pasty residues.

The corn pretreatment method known as "dry mill" is certainly very cheap per se (simple use of hammer mills), but entails the drawback of requiring high plant costs and considerable operating costs for the subsequent ethanol production plant, owing to the large amount of germ and bran that it must process.

The corn pretreatment method known as "wet mill" allows only partial reduction (on the order of 4%) of the unwanted components of corn (germ and fibers), which during the ethanol extraction step produce pasty residues that it is in any case convenient to minimize.

With respect to the "dry mill" pretreatment process described above, the "wet mill" process allows improved product quality (in terms of quantity of contained bran and fibers), but has the drawback of requiring remarkably long initial maceration steps (48 hours).

As is known, the corn grain is formed by a main part, which is known as floury kernel and is mainly composed of starch, hereinafter termed "grits", by the germ (the fatty part of the grain), and by a smaller part formed by bran (fibrous component of the grain). Pretreatment (or degermination) of corn is designed to mutually separate the above cited components of the corn grain, so as to obtain products that are as pure as possible, i.e., not contaminated by residues of the other products that are present. Examples of known methods for corn degermination are given in publications EP-A-1 213 054 and DE-OS-102 51 490.

However, the mentioned corn pretreatment systems use machines that operate very aggressively, to the point of simultaneously breaking or shredding the germ, the bran and part of the grits. For this reason, one obtains a product that from the very start of the treatment is so fine and intimately amalgamated that part of the grits is irrecoverably lost together with the bran and the germ (usually 10–15% weight of grits with respect to the weight with bran and germ). Accordingly, the secondary products, i.e., the germ and the bran, have low purity and therefore are unusable as they are, unless one resorts to the use of suitable separation systems, which entail additional costs both for the plant and for operation. Moreover, the end result in terms of lost grits in the various products depends drastically, in the plants of the background art, on the type of corn being processed.

In relation to the above pre-treatment, it is well known to mill, crushing the product between two milling surfaces which cooperate to engage the product in the middle, crushing it by the pressure that is generated by the two milling surfaces. Machines operating this way are the degerminator machine (also called dehusker or dehuller) and the pin mill. The pin mill operates at high peripheral speed of the rotating parts (about 94 m/s) and use complementary fixed pins that engage rotating pins, crushing the product in the middle. Applicant found that these machines cannot be used to achieve the advantages of the present invention, because they actually do not generate a germ and bran that could be separated in a meaningful way.

It is also known to crush the product by hammering the bulk of the product with a plurality of rotating hammers with high peripheral speed (about 94 m/s). This way the crushing of the product occurs by the increased pressure among the point where the hammer hits and the surrounding product. This also generates very strong pressure friction within the product, around the hammer, and this friction crushes the product. Applicant found that also the hammer mill cannot be used to achieve the advantages of the present invention, because, again, they actually do not allow to separate germ and bran in a meaningful way.

"Impact milling" is known in the technical field of maize crushing as a milling working on pure impact force, without increasing pressure or friction in the surrounding product. It is generally carried out with a well known machine called impactor or impact degerminator. An impactor generally has moving blades, having an impact surface, relatively large with respect to the other dimensions of the blades. The impact surface moves substantially perpendicular to the moving direction of the blades.

The above is known in the art and is described for example in the book Industria del mais, by Mario Cinquetti, 3 edition, Chiriotti editori.

EP-A-1 213 054 particularly uses, as preliminary step, degerminators with the above remarked drawbacks. In fact the use of densimetric tables is required.

U.S. Pat. No. 6,254,914 and U.S. Pat. No. 4,361,651 also uses, as preliminary step, degerminators with the above remarked drawbacks. Also this teaches soaking corn in water, particularly the ratio of corn water is preferably within the range 1–1.5 and 1–2. This involve high water consumption, the presence of expensive plant costs for decantation tanks etc, and the presence of expensive plant and maintenance systems for water distillation and recycling. Distillation require of course impressive energy costs.

U.S. Pat. No. 3,399,839 describes the use of a rotating brush with the purpose to friction the product against a drum to peel the product, without breaking it. This has the following drawbacks: it is impossible to separate a significant part of finished product, just at the beginning of the plant, to reduce the load on the whole plant, so the roller mills must be fed with the full load of product. Also, according to this teaching, the output of the roller mills is considerably unomogeneous, so that the subsequent germ extraction is more complex.

U.S. Pat. No. 6,550,700 describes a method to test maize properties in "miniature" or "micromill" simulations, which depart from the purposes of the present invention. It also describes the use of degerminators, as preliminary step, with all the above remarked drawbacks.

At this point it is added that the energy consumption of conventional corn pretreatment plants is considerable due to the power required by the individual degermination machines and for the subsequent separation step. Finally, the need of the known plant to use a machine for separating the products from the initial milled product also forces the use of personnel for constant monitoring and adjustment of the machines.

SUMMARY OF THE INVENTION

The aim of the present invention is to provide a method for producing ethanol starting from corn flours that is simple, has low plant and operating costs, can be automated easily, and allows to overcome the drawbacks of the known corn pretreatment systems described earlier. In other words, the aim of the invention is to define a method that allows to separate, at low costs, the maximum possible amounts of germ and bran, with consequent optimization of the yield of the steps of the subsequent process for obtaining ethanol, and in particular to reduce drastically the step for drying the unwanted pasty substances.

In particular, an object of the invention is to provide a method of the type described above that allows to provide the most effective separation of the components of the corn grain, reducing in particular to a minimum the losses of grits with germ and bran.

Another object of the invention is to provide a method of the described type, which starting from the source corn and regardless of its quality, allows to obtain components that have a high degree of purity.

Another object of the invention is to provide a method for producing ethanol starting from corn flours that requires reduced energy consumption, also with the possibility to automate it completely.

In accordance with the present invention, a method for producing ethanol from corn flour comprises preparing the corn flour and subsequently extracting ethanol from the prepared corn flour. The preparing of the corn flour comprises (i) impact milling corn grain, (ii) separating the impact milled corn grain into a first stream of light fractions and a second stream of germ, grits and residual bran, (iii) refining the second stream to produce refined germ, grits and residual bran, (iv) sifting the refined germ, grits and residual bran to separate germ and grits from one another, the sifting producing an intermediate product including germ, grain and residual bran, (v) refining the intermediate product, and (vi) sifting the refined intermediate product to separate germ and grits from one another.

Preferably the blades move at a speed lower than 70 m/s and more preferably lower than 35 m/s. Preferably the blades are mounted on a rotor and extend from the rotor at least 30 mm, more preferably at least 60 mm.

With respect to known systems for producing ethanol starting from corn flours, the method according to the invention allows to extract from the corn at least 7%, preferably at least 10% (by weight with respect to the initial product), of pure germ (i.e., germ that is not contaminated by other components), and at least 1% pure bran, preferably at least 2.5%, before transfer to the ethanol extraction plant, with the consequent advantages already mentioned earlier, and overcoming the drawbacks that arise from the use of the systems that constitute the currently known background art.

Especially the extraction from corn of at least 7% germ, preferably at least 10%, and of at least 1% bran, preferably at least 2.5%, allows to obtain drastic reductions in the production of pasty residues in the subsequent ethanol extraction process.

With respect to conventional systems, the system according to the invention offers in particular the advantage:

of separating effectively and selectively the individual components, so as to simplify and increase the speed of the subsequent separation actions during the ethanol production process;

of not being affected by the quality of the source corn in terms of separation yield;

of reducing the energy consumption involved in the overall degermination treatment, also allowing to automate the entire plant.

This aim and these and other objects, advantages and characteristics are apparent from the detailed description that follows of a preferred embodiment of the method according to the invention, illustrated by way of non-limiting example in the accompanying drawing.

DETAILED DESCRIPTION OF THE INVENTION

Figures 1, 2:
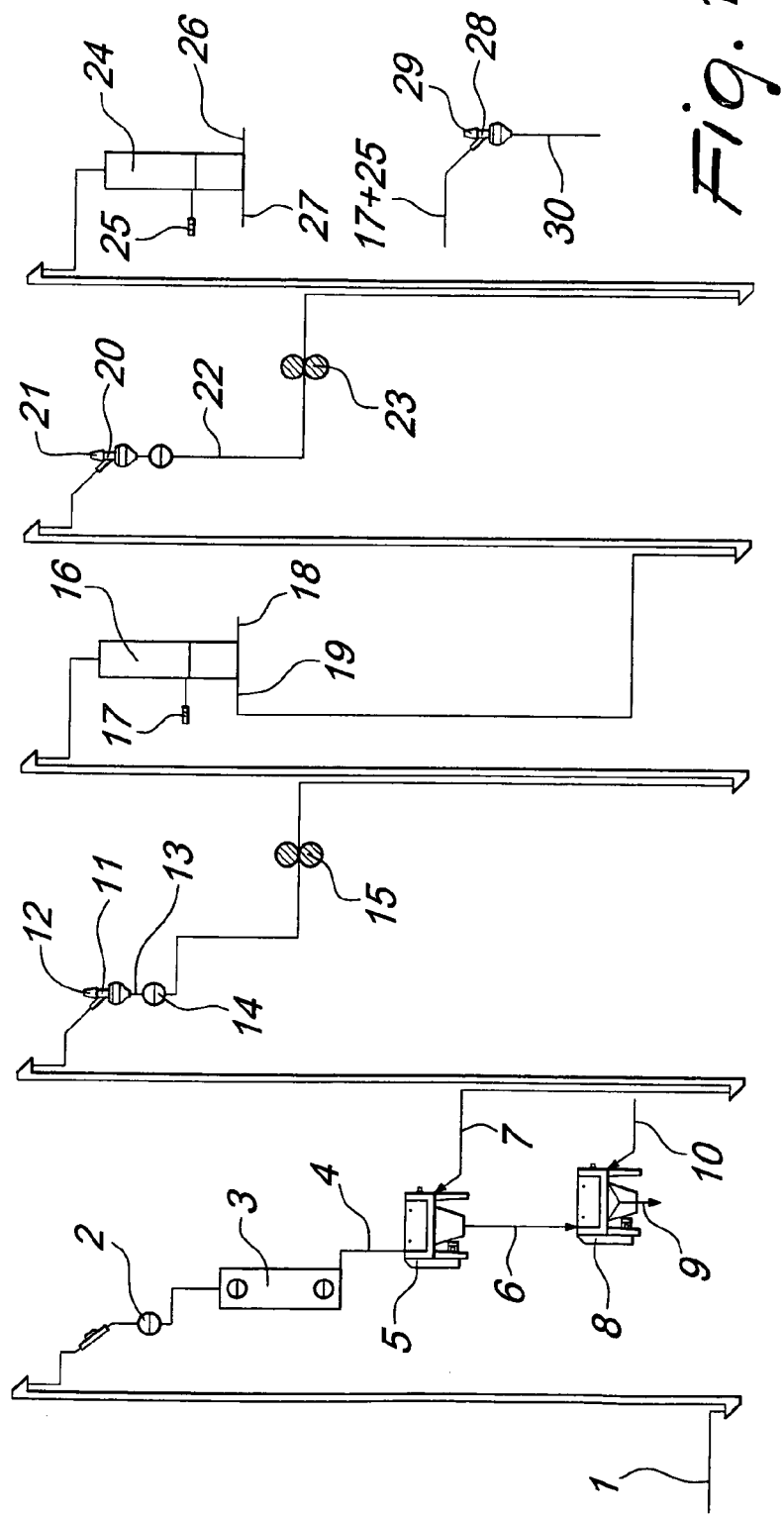
FIG. 1 is a flow diagram illustrating the process of the present invention.
FIG. 2 is a flow diagram illustrating further operations on output streams from the process of FIG. 1.
Figure 3:
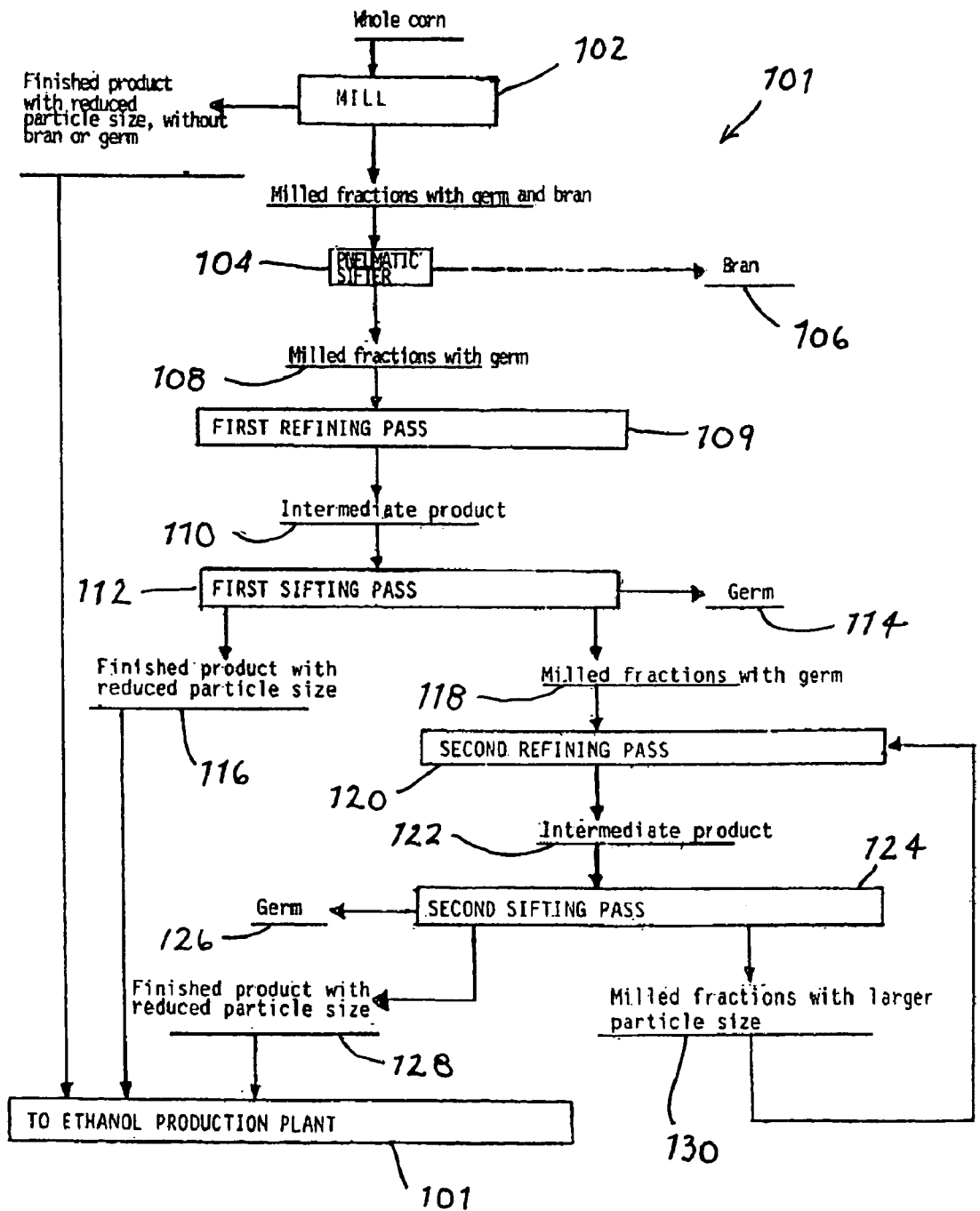
FIG. 3 is a flow diagram depicting steps in the preparing of corn flours, in a method pursuant to the present invention.

As depicted in FIG. 3, the present method for producing ethanol from corn flour comprises preparing the corn flour 100 and subsequently extracting ethanol from the prepared corn flour in an ethanol production plant 101. The preparing of the corn flour comprises impact milling corn grain (step 102 in FIG. 3) and separating, in a step 104, the impact milled corn grain into a first stream 106 of light fractions and a second stream 108 of germ, grits and residual bran. The preparing of the corn flour further comprises refining the second stream 108 in a step 109 to produce an intermediate product 110 of refined germ, grits and residual bran, and sifting the refined germ, grits and residual bran in a step 112 to separate germ 114 and grits 116 from one another. The sifting 112 produces an intermediate product 118 (milled fractions) including germ, grain and residual bran. The intermediate product is refined in a step 120 to produce another intermediate product 122. The refined intermediate product 122 is sifted in a step 124 to separate germ 126 and grits 128 from one another. Milled fractions 130 with larger particle sizes may be recycled for further treatment.

The method according to the invention begins with the treatment of the feed 1 of corn in a first station 2 for wetting with water. Water is added in an amount equal to 0.5–1.0% by weight, keeping inactive in a tank 3 for approximately 60 minutes. The wet corn 4 that exits from the tank 3 feeds an impactor 5, the fundamental purpose of which is to break the corn in multiple pieces, allowing to keep the greatest average particle size of the milled fractions, by impact action, also ensuring minimum friction that cooperates to detach the bran.

During this step, the germ, which is rendered even more elastic by the previous wetting treatment, separates from the grits. It is stressed that the impact milling, provided for example by means of a mill with rotating vanes or the like, is designed to break up the corn grain very coarsely, leaving the germ intact, so as to prevent its breakage from increasing the difficulty in separating the grits, compromising the final yield of the degermination process.

Accordingly, throughs 6, formed by coarse pieces of the corn grain, which still have, all together, part of their original components, and a reject 7, constituted by the same material that forms the throughs 6 but larger, are then separated by the mill 5.

The throughs 6 in output from the mill 5 are sent to a first rotating separator 8, which separates the grits 9 from the throughs 6 and a corresponding waste 10, formed by grits, germ and bran. The reject 7 that arrives from the mill 5 is sent to a first pneumatic separator 11, from which there exit a stream 12 of lightweight parts, constituted by bran and any fine parts of grits entrained by the stream of the main product, and a stream 13 of grits, germ and residual bran. The stream 13 is then sent to a second station 14 for wetting with water and then to a first roller mill 15, in which the germ is crushed so as to facilitate subsequent size separation in the first sieve 16. During milling in the roller mill 15, a further size reduction of the grits also occurs, which by virtue of its solid nature (different from the plastic nature that characterizes the germ) tends to break up due to the crushing action.

In output from the sieve 16 there is an output 17 of germ as a finished product, an output 18 of grits as a finished product, and an output 19 of intermediate product. The intermediate product stream 19, added to the waste 10 that arrives from the rotary separator 8, is made to pass through a second pneumatic separator 20, from which a stream 21 of lightweight parts, constituted by bran plus additional fine pieces of grits, and a stream 22 of grits, germ and smaller quantities of residual bran, flow out.

The stream 22 of grits is sent to a second roller mill 23, in which the germ is crushed once again, so as to facilitate its subsequent size separation in the second sifter 24. Further size reduction of the grits is performed in the roller mill 23. In output from the second sieve 24 there is an output 25 of germ as a finished product, an output 26 of grits as a finished product, and an output 27 of intermediate product; the intermediate product is to be sent to recycling on the roller second mill 23. The germ outputs 17 and 25, which originate respectively form the sieves 16 and 24, are conveyed to a third pneumatic separator 28, from which a current of light fractions 29 (only bran) and a current of germ 30 separate.

The light fractions 12 from the separator 11, the light fractions 21 from the separator 20 and the light fractions 29 from the separator 28 are conveyed to a pneumatic settling unit 31, from which an output 32 of bran and any fine grits fractions and an output 33 of dusty air to be sent to the bag filter 34 flow out. The output 32 is sent to a second rotary separator 35, which divides the stream 32 into a grits output 36 and a corresponding reject 37 formed by bran. The grits output 38 that arrives from the air current 33 also separated in the same filter 34.

According to a different embodiment of the invention, it is possible to provide a single milling in the mill 5 and a single milling in the roller mill 15 associated sifting in the sieve 16.

According to a further different way of carrying out the invention, it is possible to provide a single milling and three or more passes for refining (milling) and corresponding sifting.

The corn flour obtained in the manner described above subsequently enters the appropriately provided ethanol extraction plants, in which a chemical process is performed which substantially has the following steps:

Baking-Gelatinizing

In order to start conversion into ethanol of the starches contained in the source product, the cereal that constitutes the raw material must be rendered easier to attack by the enzymes used in the subsequent steps. This result is achieved by baking the source cereal. All the output product of this step is the input of the subsequent step.

Dextrinization-Saccharification

The gelatinized starch obtained from the baking step is subjected to the degrading action on the part of amylolytic enzymes, with the corresponding production of fermentable sugars. All of the product in output from this step constitutes the input of the subsequent step.

Fermentation

Yeasts (specifically saccharomycetes) are added in this step of the process. During fermentation, the sugars contained in the source cereal are converted into ethanol and carbon dioxide. The ethanol in output from this step constitutes the input of the next step.

Distillation

During this step, 95° proof ethanol and pasty residues are obtained. The ethanol and the pasty residues are transferred to different drying steps.

Ethanol Drying

This step produces the actual finished product, i.e., 99.995° proof ethanol.

Residue Drying

The pasty residues obtained during the distillation step are centrifuged and dried, obtaining products with 90% dry substance usable for zootechnical use.

Figure 4:
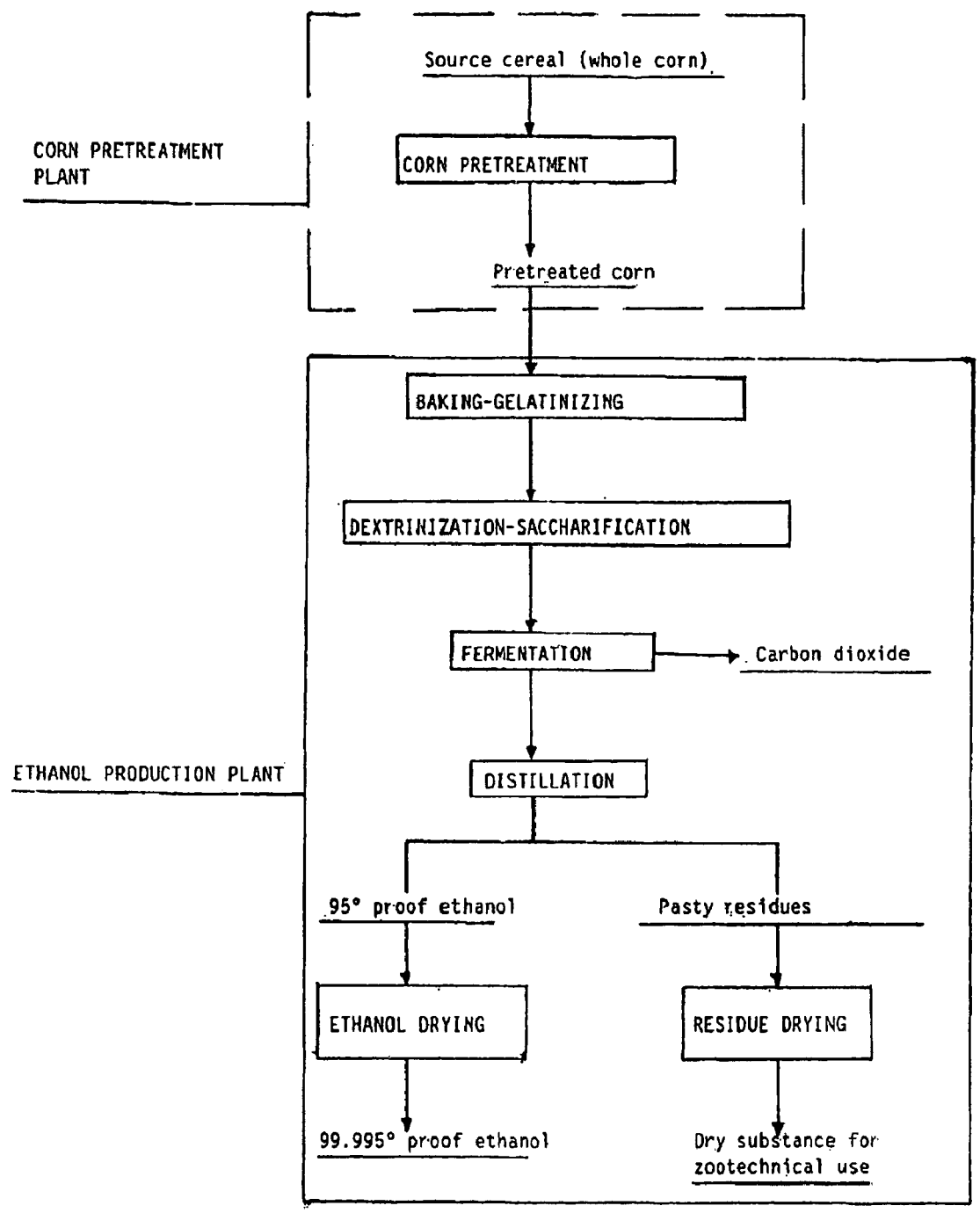
FIG. 4 is a flow diagram depicting steps in the extracting of ethanol from corn flours as produced by the method of FIG. 3.

The actual process for extracting ethanol from the corn flour, as obtained in the manner described above, is shown schematically in FIG. 4.

Preferred ways of carrying out the invention are given in the examples that follow, which are provided merely by way of example.

Practical tests on the system were conducted in an industrial plant with a capacity of 4000 kg/h.

The corn 1 that was used, having the characteristics described below, was treated by adding 40 l/h of water 2, and the treatment time of the corn in the tank 3 after adding water was 55 minutes, so as to reach a final humidity of 12.40%.

The characteristics of the dry corn at test time were as follows:

| | |
|---|---|
| Humidity | 11.40% |
| Ash | 1.47% on the dry substance |
| Protein | 10.00% on the dry substance |
| Fats | 4.06% on the dry substance |
| Starches | 74.50% on the dry substance |

Once the intended resting time has elapsed, the extracted product 4 feeds the mill 5 with a capacity of 3950 kg/h.

The reject 7 and the throughs 6 of the mill 5 are respectively 2936 kg/h as the coarse fraction part and 1014 kg/h as a fine fraction. The particle sizes of the products related to the two fractions are:

| | Reject 7% | Throughs 6% |
|---|---|---|
| 5000 microns | 27.0 | 0.0 |
| 4000 microns | 11.0 | 0.0 |
| 3600 microns | 29.0 | 6.0 |
| 2600 microns | 29.0 | 49.0 |
| 2000 microns | 0.5 | 5.0 |
| 1000 microns | 2.0 | 20.0 |
| 500 microns | 0.5 | 10.0 |
| Throughs | 1.0 | 10.0 |

As shown in the accompanying drawing, the throughs 6 are further graded in the first rotary separator 8, from which 64 kg/h of product 9 are separated, while the remaining reject 10, equal to 948 kg/h, is conveyed to the second pneumatic separator 20. The difference between the input product, equal to 2 kg/h, can be considered as a milling loss caused by evaporation.

The reject 7 from the mill 5, equal to 2936 kg/h, before being sent to the roller mill 15, passes through a pneumatic separator 11, which separates 137 kg/h of light product 12 by means of an air stream.

The remaining product 13, equal to 2799 kg/h, is treated by adding water in a second wetting station 14, equal to 12 l/h without resting, so as to reach a humidity level of 11.80%, and is then milled through the first roller mill pass 15, where it arrives at the output with the following particle size distribution:

| Particle size | % |
|---|---|
| 4500 microns | 7–8 |
| 2500 microns | 10–13 |
| 2000 microns | 25–30 |
| 1500 microns | 30–35 |
| 700 microns | 7–10 |
| 800 microns | 3–5 |
| Throughs | 1–2 |

As shown in the description, germ separation occurs by size difference in the sieve 16, in which the following 3270-micron sifters are fitted. The grades provided in the sieve 16 are three, and the separated quantities are:

Germ 17 equal to 273 kg/h

Intermediate product 19 equal to 1337 kg/h

Grits 18 equal to 1165 kg/h

The difference, with respect to the product in input to the roller mill 15, equal to 23 kg/h, can be considered as a milling loss caused by evaporation.

In this step of the process, the germ 17 is separated by means of 3270-micron screens, while the grits 18 are passed through 1800-micron screens. Both products are removed from the milling process. The intermediate product 19 comprised between 3270 and 1800 microns, equal to 1337 kg/h, is the product that will then load the pneumatic separator 20.

The second roller mill pass 23 is loaded simultaneously with the product 10 that arrives from the turbosifter, which is equal to 948 kg/h, and with the reject 19 of the sieve 16 used for the passage of B1, which is equal to 1337 kg/h, for a total of 2285 kg/h. The pneumatic separator 20 is loaded with the reject 10 (948 kg/h) and with the intermediate product 19 (1337 kg/h), for a total of 2285 kg/h. In this case also, the product, before feeding the roller mill 23, passes through the second pneumatic separator 20, which separates the light fractions 21. The amount of separated light product is 123 kg/h.

The product 22, with a flow-rate of 2162 kg/h together with 221 kg/h of product 27 returned from the sieve 24, after milling through the roller mill pass 23, has the following output particle size distribution:

| Particle size | % |
|---|---|
| 3200 microns | 3–4 |
| 2500 microns | 5–8 |
| 1500 microns | 30–35 |
| 700 microns | 35–40 |
| 300 microns | 8–12 |
| Throughs | 2–3 |

The following products are obtained after the gradings that occur in the sieve channel 24:
Germ 25 equal to 115 kg/h
Intermediate product 27 equal to 221 kg/h
Grits 26 equal to 2039 kg/h The difference with respect to the product in input, equal to 8 kg/h, can be considered as a milling loss due to evaporation.

In this pass, the germ is separated as reject 25 on 1800-micron screens, while the grits 26 are passed at 1180 microns. The intermediate product 27 is passed by 1180–1800 micron sifters. The total grits collected in the various steps of the product amount to 3441 kg/h, equal to 86.02%.

The characteristics of the end product 9+18+26+36 +38 are:

| | |
|---|---|
| Humidity | 12.40% |
| Ash | 0.683% on the dry substance |
| Protein | 8.74% on the dry substance |
| Fats | 1.680% on the dry substance |
| Starches | 80.40% on the dry substance |

The germ 17+25, before being considered a finished product, passes through a separator 28, the purpose of which is to remove any light fractions 29 present in the germ. The amount of light fractions 29 separated during this step is 11 kg/h. As regards the germ, the total 30 of the final clean germ is 377 kg/h, equal to 9.42%.

The characteristics of the resulting end product are:

| | |
|---|---|
| Humidity | 9.70% |
| Ash | 8.23% on the dry substance |
| Protein | 19.75% on the dry substance |
| Fats | 25.80% on the dry substance |
| Starches | 15.80% on the dry substance |

The air mixture that contains the light fractions 12, 21 and 29, for a total of 271 kg/h, passes through the pneumatic settling unit 31, where the heavier product 32 (bran and fine grit fractions) amounts to 176 kg/h. This product 32 is then treated in the rotary separator 35, which separates the bran 37 from the grits 36.

The amount of separated bran 37 is equal to 85 kg/h, with the characteristics described above. The remaining fraction of the product 36, equal to 88 kg/h, is considered as a finished product (grits) to be collected and mixed with the products that arrive from other destinations.

The difference with respect to the product in input 32, equal to 3 kg/h, can be considered as milling loss caused by evaporation.

The characteristics of the separated bran 37, equal to 2.12%, are:

| | |
|---|---|
| Humidity | 9.34% |
| Ash | 0.790% on the dry substance |
| Protein | 6.85% on the dry substance |
| Fats | 5.040% on the dry substance |
| Starches | 14.48% on the dry substance |

The grits 38 that arrive from the filter 34, equal to 85 kg/h, are considered as grits and therefore must be mixed with the grits that arrive from other points.

Laboratory analyses show that the laboratory results confirm the described process.

| Summary of flow rates | |
|---|---|
| Grits 18 from the sieve 16 | 1165 kg/h |
| Grits 26 from the sieve 24 | 2039 kg/h |
| Grits 9 from the separator 8 | 64 kg/h |
| Grits 36 from the separator 35 | 88 kg/h |
| Grits 38 from the filter 34 | 85 kg/h |

Total extracted grits: 3441 kg/h, equal to 86.02% by weight with respect to the feed 1.

| | |
|---|---|
| Bran 37 | 85 kg/h, equal to 2.13% |
| Germ 30 | 377 kg/h, equal to 9.43% |
| Milling loss | 97 kg/h, equal to 2.42% |
| By feeding the ethanol extraction plant with 4000 kg/h of corn treated according to the known art ("dry mill") one obtains in input: | |
| corn | 4000 kg/h |
| composed of: | |
| 74% starches giving a total of | 2960 kg/h of starches |
| 26% germ, bran and associated components, giving a total of | 1040 kg/h of germ, bran |
| while in output one obtains: | |
| ethanol | 416 gallons/h |
| dried pasty product plus carbon dioxide. | 1040 kg/h |
| By feeding the ethanol extraction plant with 4000 kg/h of grits of corn treated according to the present invention, one obtains in input: | |
| corn grits | 4000 kg/h |
| composed of: | |
| 86% starches giving a total of | 3440 kg/h of starches |
| 14% germ, bran and associated components, giving a total of | 560 kg/h of germ, bran |
| while in output one obtains: | |
| ethanol | 483 gallons/h |
| dried pasty product plus carbon dioxide. | 560 kg/h |

The example shows that the use of corn flours obtained according to the method of the present invention allows to obtain, in the subsequent ethanol production process, a higher yield and a lower amount of pasty product to be dried, with a consequent energy saving.

The invention claimed is:
1. A method for producing ethanol from corn flour, comprising preparing the corn flour and subsequently extracting ethanol from the prepared corn flour, the preparing of the corn flour comprising:
- impact milling corn grain;
- separating the impact milled corn grain into a first stream of light fractions and a second stream of germ, grits and residual bran;
- refining said second stream to produce refined germ, grits and residual bran;
- sifting the refined germ, grits and residual bran to separate germ and grits from one another, the sifting producing an intermediate product including germ, grain and residual bran;
- refining the intermediate product; and
- sifting the refined intermediate product to separate germ and grits from one another.

2. The method according to claim 1, wherein said impact milling is carried out on wet corn grain, so as to preserve a largest possible average particle size of milled fractions in said second stream, with separation of the bran by friction.

3. The method according to claim 2, wherein the refining of said second stream includes crushing of the germ, so as to facilitate its size separation.

4. The method according to claim 1, wherein said impact milling is carried out using an impactor.

5. The method according to claim 4, wherein said impactor has moving blades, having an impact surface, relatively large with respect to the other dimensions of the blades; said impact surface moving substantially perpendicular to a moving direction of said blades.

6. The method according to claim 5 in which said blades move at a speed lower than 70 m/s.

7. The method according to claim 6 in which said blades are mounted on a rotor and extend from the rotor at least 30 mm.

8. The method according to claim 1, wherein throughs in output from said impact milling are sent to a rotary separator, which separates the grits from the throughs and a corresponding reject.

9. The method according to claim 8, wherein said impact milling produces a reject stream is sent to a first separator, from which said first stream of light fractions and said second stream of grits, germ and residual bran exit, said second stream being subsequently sent to a station for wetting with water and to a first roller mill, in which the germ is crushed, so as to facilitate subsequent size separation of germ and grits in a sieve, the sifting of the refined germ, grits and residual bran and the producing of said intermediate product taking place via said sieve.

10. The method according to claim 9, wherein said intermediate product in output from the sieve is added to the reject from the rotary separator and is passed through an additional separator, from which a third stream of light fractions and a fourth stream of grits, germ and minor amounts of residual bran exits.

11. The method according to claim 10, wherein said fourth stream is sent to a second roller mill, in which additional crushing of the germ in said fourth stream is performed so as to facilitate subsequent size separation in an additional sieve.

12. The method according to claim 11, further comprising, in output from said additional sieve, an output of germ as a finished product, an output of grits as a finished product, and an output of additional intermediate product, in which the germ outputs, which arrive respectively from the sieves, are conveyed to a yet another separator, from which a stream of light fractions and a stream of germs separate.

13. The method according to claim 9, wherein the refining of said second stream generates an additional light fraction stream, further comprising conveying said first stream and said additional light fraction stream to a pneumatic settling unit, from which a first output for bran and any fine grits fractions and a second output of dusty air lead out, also comprising conveying said air in turn into a manifold to be sent to a bag filter.

14. The method according to claim 13, wherein said first output leads to a rotary separator, which divides the bran and fine ants fractions of said first output into a grits output and a corresponding waste formed by bran, grits in the dusty air of said second output being further separated in said filter.

15. The method according to claim 5 in which said blades move at a speed lower than 35 m/s.

16. The method according to claim 6 in which said blades are mounted on a rotor and extend from the rotor at least 60 mm.

* * * * *